United States Patent [19]

Davis

[11] Patent Number: 4,751,330

[45] Date of Patent: Jun. 14, 1988

[54] PROCESS FOR PREPARING (HYDROCARBYLTHIO) AROMATIC AMINES

[75] Inventor: Robert L. Davis, Baton Rouge, La.

[73] Assignee: Ethyl Corporation, Richmond, Va.

[21] Appl. No.: 26,828

[22] Filed: Mar. 17, 1987

Related U.S. Application Data

[63] Continuation-in-part of Ser. No. 796,200, Nov. 8, 1985, abandoned.

[51] Int. Cl.[4] .................................. C07C 149/42
[52] U.S. Cl. ............................. 564/440; 564/307; 564/335; 564/427; 564/428; 564/430; 546/290; 548/337; 548/484; 548/541
[58] Field of Search ............... 564/307, 335, 427, 428, 564/430, 440; 546/290; 548/337, 484, 541

[56] References Cited

U.S. PATENT DOCUMENTS

| | | | |
|---|---|---|---|
| 4,594,453 | 6/1986 | Ranken et al. | 564/440 |
| 4,670,597 | 6/1987 | Ranken et al. | 564/307 |
| 4,670,598 | 6/1987 | Davis | 564/307 |

OTHER PUBLICATIONS

Bliznyuk et al, *Chemical Abstracts*, vol. 101, No. 152080t (1984).

*Primary Examiner*—Glennon H. Hollrah
*Assistant Examiner*—John A. Sopp
*Attorney, Agent, or Firm*—Patricia J. Hogan

[57] ABSTRACT

(Hydrocarbylthio)aromatic amines are prepared by reacting an aromatic amine, such as an aminobenzene, with a hydrocarbyl disulfide, such as an alkyl disulfide, in the presence of a metal or metal halide catalyst and iodine as a promoter.

15 Claims, No Drawings

4,751,330

PROCESS FOR PREPARING (HYDROCARBYLTHIO) AROMATIC AMINES

CROSS-REFERENCE TO RELATED APPLICATION

This application is a continuation-in-part of copending application Ser. No. 796,200, filed Nov. 8, 1985 now abandoned.

FIELD OF INVENTION

This invention relates to (hydrocarbylthio)aromatic amines and more particularly to a process for preparing them.

BACKGROUND

As disclosed in U.S. Pat. No. 4,594,453 (Ranken et al.), it is known that various (hydrocarbylthio)aromatic amines are useful as intermediates in the preparation of biologically-active materials, polyurethanes, etc.; and they can be prepared by reacting an aromatic amine with a hydrocarbyl disulfide in the presence of a catalytic amount of a Lewis acid. The preferred catalysts of Ranken et al. are metal halides, such as aluminum chloride, boron trifluoride, boron trichloride, ferric chloride, and zinc chloride.

In the case of at least some aromatic amines, it has been found that the preferred catalysts identified by Ranken et al. have the disadvantages of effecting the desired hydrocarbylthiations at too slow a rate to be completely satisfactory and of sometimes providing too low a yield of product.

SUMMARY OF INVENTION

An object of this invention is to provide a novel process for preparing (hydrocarbylthio)aromatic amines.

Another object is to provide such a process wherein the products are prepared by the hydrocarbylthiation of aromatic amines in the presence of metal or metal halide catalysts.

A further object is to provide such a process wherein the reaction rates and/or product yields are improved.

These and other objects are attained by reacting an aromatic amine with a hydrocarbyl disulfide in the presence of iodine and a catalytic amount of a metal or metal halide.

DETAILED DESCRIPTION

Aromatic amines utilizable in the practice of the invention include:

(1) compounds having at least one amino group attached to a carbocyclic or heterocyclic ring of an aromatic compound containing one or more simple and/or fused rings, such as benzene, naphthalene, anthracene, pyrrole, pyridine, indole, etc., rings and (2) reactive heterocyclic amines, such as pyrrole, indole, imidazole, etc.

The compounds may bear no substituents other than the required amino group, or they may bear substituents inert to the reaction conditions, such as one or more additional amino groups or substituents such as chloro, fluoro, alkyl, alkoxy, alkylthio, aryl, aryloxy, arylthio, alkaryl, or aralkyl groups on any positions other than those to be substituted by hydrocarbylthio groups. In the case of coupled aromatic rings, the rings may be directly attached to one another or may be coupled through a bridge such as an oxygen, sulfur, sulfoxide, sulfone, alkyl, or other hydrocarbon link.

Useful aromatic amines include, e.g., 4,4'-methylenedianiline, 2-aminobiphenyl, 1,3-dimethylpyrrole, 1-methylpyrrole, 7-methylindole, aminobenzenes containing one or two amino groups, such as aniline, 3-methylaniline, 4-methylaniline, 4-chloroaniline, 4-(phenylthio)aniline, 4-phenoxyaniline, 2-ethylaniline, N-methylaniline, 2,4- and 2,6-diaminotoluenes, 2,6-diamino-1-ethyl-benzene, etc.

Hydrocarbyl disulfides which may be reacted with the aromatic amines include saturated and unsaturated aliphatic, cycloaliphatic, and aromatic disulfides in which the hydrocarbyl groups optionally bear inert, such as chloro, substituents. Exemplary of such compounds are methyl, ethyl, propyl, n-butyl, sec-butyl, t-butyl, 2-chloropentyl, cyclopentyl, cyclohexyl, phenyl, benzyl, p-tolyl, and p-chlorophenyl disulfides, etc. This component of the reaction mixture is generally employed in at least the stoichiometric amount required to yield the desired (hydrocarbylthio)aromatic amine, i.e., at least an equimolar amount being used when a mono(hydrocarbylthio)aromatic amine is desired, at least two molar equivalents being utilized when a di(hydrocarbylthio)aromatic amine is desired, etc.

The reaction of the aromatic amine with the hydrocarbyl disulfide is generally conducted at a temperature in the range of about 20°–300° C., preferably about 100°–200° C., and at a pressure of atmospheric up to about 1000 psi; and, as mentioned above, it is conducted in the presence of iodine and a catalytic amount of a metal or metal halide.

Metals and metal halides which can have their catalytic activity enhanced by the practice of the invention are the known Lewis acid catalysts, such as those mentioned in Ranken et al. and similar compounds, e.g., aluminum chloride, ferric chloride, ferrous chloride, cupric chloride, chromic chloride, zinc chloride, lead chloride, mercurous chloride, the corresponding metal bromides, iodides, and fluorides, the corresponding metal powders, etc. Particularly good results are obtained when copper, zinc, or ferric, ferrous, or aluminum chloride is used. The catalyst is employed in catalytic amounts, generally in a catalyst/aromatic amine mol ratio of about 0.01–0.5/1, preferably about 0.01–0.2/1. The iodine employed as a promoter is also used in catalytic amounts, generally in an iodine/metal or metal halide mol ratio of about 0.05–2/1, preferably about 0.05–1.5/1.

In conducting the process of the invention, it is frequently preferred to (1) heat a mixture of the catalyst, iodine, and aromatic amine at a suitable temperature, usually a temperature higher than the boiling point of the disulfide to be added, e.g., about 100°–150° C., until all of the catalyst has reacted and then (2) heat the reaction mixture at reflux temperature after the disulfide has been added to effect a hydrocarbylthiation process while removing evolved hydrocarbyl thiol by-product from the reaction vessel. However, it is also satisfactory to conduct the process by simply mixing the catalyst, iodine, and reactants together and heating them to the reflux temperature. An inert solvent may be employed if desired but is unnecessary.

The process of the invention, like the process of Ranken et al., results in the formation of (hydrocarbylthio)aromatic amines which are useful as intermediates in the preparation of biologically-active materials, polyurethanes, etc. It is particularly advantageous in that it is characterized by higher reaction rates and/or higher yields than are obtained when the iodine promoter is not employed.

The following examples are given to illustrate the invention and are not intended as a limitation thereof.

COMPARATIVE EXAMPLE A

A suitable reaction vessel was charged with one molar proportion of aniline and 0.067 molar proportion of aluminum chloride. After the reaction mixture had been stirred in a nitrogen atmosphere at 150° C. for 30 minutes and cooled to 100° C., one molar proportion of methyl disulfide was added. The reaction mixture was then stirred and heated at an initial reflux temperature of 130° C. to a final temperature of 170° C. in 25 hours to provide a crude reaction product which was cooled, worked up, and analyzed by gas chromatography, using n-undecane as an internal standard. The analysis showed that the reaction mixture contained 14 wt% methyl disulfide, 19 wt% aniline, 18 wt% 2-(methylthio)aniline, 33 wt% 4-(methylthio)aniline, and 7 wt% 2,4-di(methylthio)aniline.

EXAMPLE I

Comparative Example A was essentially repeated except that 0.0085 molar proportion of iodine was added to the initial reaction mixture, and the reflux time required was only 7 hours instead of 25 hours. The reaction resulted in the formation of a reaction mixture containing 12 wt% methyl disulfide, 16 wt% aniline, 17.5 wt% 2-(methylthio)aniline, 37 wt% 4-(methylthio)aniline, and 11.2 wt% 2,4-di(methylthio)aniline.

COMPARATIVE EXAMPLE B

One molar proportion of commercial toluenediamine (c-TDA)—a material containing 80% 2,4-diaminotoluene and 20% 2,6-diaminotoluene—was heated with 0.065 molar proportion of aluminum chloride at 150° C. for one hour. Methyl disulfide was then added in sufficient excess to maintain the reaction temperature at 135° C., and the reaction was conducted for 39 hours to achieve 100% conversion of the c-TDA. Analysis of the product showed it to contain 16 mol% mono(methylthio) derivatives of c-TDA (MMTDA), 78 mol% di(methylthio) derivatives of c-TDA (DMTDA), and 6 mol% by-products.

EXAMPLE II

Comparative Example B was essentially repeated except that the initial reaction mixture contained one molar proportion of c-TDA, 0.068 molar proportion of aluminum chloride, and 0.0032 molar proportion of iodine, and the reaction time required to reach 100% conversion was only 22 hours. The product contained 10 mol% MMTDA, 83 mol% DMTDA, and 6 mol% by-products.

EXAMPLE III

Each of nine reactions was conducted essentially as described in Comparative Example B except for using, respectively:

| Reaction | Catalyst | Molar Proportions |
|---|---|---|
| III-1 | FeCl$_3$/I$_2$ | 0.05/0.0066 |
| III-2 | FeCl$_2$/I$_2$ | 0 05/0.0066 |
| III-3 | CrCl$_3$/I$_2$ | 0.05/0.0066 |
| III-4 | CuCl$_2$/I$_2$ | 0.05/0.0033 |
| III-5 | Fe/I$_2$ | 0.05/0.05 |
| III-6 | Zn/I$_2$ | 0.05/0.05 |
| III-7 | Zn/I$_2$ | 0.05/0.05 |
| III-8 | Cu/I$_2$ | 0.05/0.025 |
| III-9 | Cu/I$_2$ | 0.05/0.025 | instead of the 0.065 molar proportion of aluminum chloride. The reaction times required, the conversions obtained, and the percentages of MMTDA and DMTDA in the final product are shown below.

| Rxn. | Metal Cat. | Time (Hrs.) | Conversion (%) | % Yield MMTDA | % Yield DMTDA |
|---|---|---|---|---|---|
| III-1 | FeCl$_3$ | 18 | 100 | 13 | 84 |
| III-2 | FeCl$_2$ | 18 | 100 | 12 | 87 |
| III-3 | CrCl$_3$ | 16 | 100 | 14 | 77 |
| III-4 | CuCl$_2$ | 24 | 98 | 28 | 71 |
| III-5 | Fe | 10 | 87 | 78 | 22 |
| III-6 | Zn | 18 | 100 | 26 | 72 |
| III-7 | Zn | 22 | 100 | 18 | 81 |
| III-8 | Cu | 7 | 100 | 9 | 90 |
| III-9 | Cu | 10 | 100 | 6 | 92 |

EXAMPLE IV

Three reactions were conducted by essentially repeating Reaction III-9 except for varying the amount of iodine to provide different Cu/I ratios. In each reaction, 100% conversion was obtained in 10 hours. The Cu/I ratios used and the percentages of MMTDA and DMTDA in the final product are shown below

| Cu/I | % Yield MMTDA | % Yield DMTDA |
|---|---|---|
| 1/1.6 | 7 | 87 |
| 1/1.3 | 6 | 90 |
| 1/0.7 | 11 | 89 |

It is obvious that many variations may be made in the products and processes set forth above without departing from the spirit and scope of this invention.

What is claimed is:

1. In a process for reacting an aromatic amine with a hydrocarbyl disulfide in the presence of a catalytic amount of a metal or metal halide to form a (hydrocarbylthio)aromatic amine, the improvement which comprises conducting the reaction in the presence of iodine as a promoter.

2. The process of claim 1 wherein the aromatic amine is an aminobenzene.

3. The process of claim 2 wherein the aminobenzene is aniline.

4. The process of claim 2 wherein the aminobenzene is a diaminobenzene.

5. The process of claim 4 wherein the diaminobenzene is a diaminotoluene.

6. The process of claim 1 wherein the hydrocarbyl disulfide is an alkyl disulfide.

7. The process of claim 6 wherein the alkyl disulfide is methyl disulfide.

8. The process of claim 1 wherein the catalyst is a metal powder.

9. The process of claim 8 wherein the metal is zinc.

10. The process of claim 8 wherein the metal is copper.

11. The process of claim 1 wherein the catalyst is a metal halide.

12. The process of claim 11 wherein the metal halide is a metal chloride.

13. The process of claim 12 wherein the metal chloride is aluminum chloride.

14. The process of claim 12 wherein the metal chloride is ferric chloride.

15. The process of claim 12 wherein the metal chloride is ferrous chloride.

* * * * *